United States Patent [19]

Doyle et al.

[11] Patent Number: 5,081,286
[45] Date of Patent: Jan. 14, 1992

[54] PROCESS FOR THE PREPARATION OF AN ALKYL METHACRYLATE

[75] Inventors: Michael J. Doyle; Johan Van Gogh; Johan C. Van Ravenswaay Claasen, all of Amsterdam, Netherlands

[73] Assignee: Shell Oil Company, Houston, Tex.

[21] Appl. No.: 506,146

[22] Filed: Apr. 9, 1990

[30] Foreign Application Priority Data

Apr. 11, 1989 [GB] United Kingdom ............... 8908079
Mar. 16, 1990 [GB] United Kingdom ............... 9005963

[51] Int. Cl.$^5$ ............................................. C07C 67/36
[52] U.S. Cl. ..................................... 560/206; 560/207; 562/522
[58] Field of Search ................ 560/206, 207; 502/522

[56] References Cited

U.S. PATENT DOCUMENTS 3,709,927 1/1973 Kunichikas et al. ............... 560/206

OTHER PUBLICATIONS

Haeberle and Emig, "Kinetic Investigation ...," Chem. Eng. Technol. 11 (1988) pp. 392–402.
Sakakibara, "Synthesis of Methacrylic Esters ....," Chemical Society of Japan, pp. 1601–1609 (1964).
Kirk–Othmer Ency., "Methylacetylene," pp. 547–556.

*Primary Examiner*—Paul J. Killos

[57] ABSTRACT

A process for the preparation of an alkyl methacrylate, which process comprises:

a) selectively removing propadiene from a $C_3$-mixture comprising a mixture of propyne and propadiene that has been obtained from an ethene cracker, a catalytic cracker or an LPG-dehydrogenation process, to provide a propyne feed in which the ratio of propyne to propadiene is at least about 6:1, nd b) contacting the propyene feed with carbon monoxide and an alkanol in the presence of a carboxylation catalyst.

25 Claims, No Drawings

5,081,286

PROCESS FOR THE PREPARATION OF AN ALKYL METHACRYLATE

BACKGROUND OF THE INVENTION

The present invention relates to a process for the preparation of an alkyl methacrylate. In a specific aspect, the invention relates to a process for preparing methyl methacrylate.

Methyl methacrylate is prepared in industry mainly by the acetone cyanohydrin process. This process presents disadvantages in that large quantities of waste sulphuric acid and ammonium bisulphate are produced, and these by-products must be discharged or worked up for reuse. Another by-product, HCN, is highly toxic and raises difficult problems of storage and transportion. As concerns about the environment have increased, considerable research has been devoted to finding alternative processes which do not present these disadvantages.

One possible alternative process, described in 1964 by Y. Sakakibira in Bull. Chem. Soc. Japan 37, 11 (1964) 1601–1609, involves the reaction of propyne with carbon monoxide and alkanol in the presence of a carboxylation catalyst. Although this process has been known for a long time and has attracted a considerable amount of interest, it has never been commercialized.

A factor inhibiting the commercial exploitation of the carboxylation process has been the unavailability of large quantities of a suitable low-priced propyne feed.

Many processes have been described for the preparation of propyne. For example, the chapter "Methylacetylene" in Kirk-Othmer's Encyclopedia of Chemical Technology, 2nd ed., Volume Supplement (1971), pages 547 to 556, refers to various processes including the dehydrohalogenation of propylene dibromide, the hydration of magnesium carbide, the reaction of sodium acetylide and dimethylsulphate in liquid ammonia, and a variety of pyrolysis or cracking methods.

European patent application publication number EP-A-0190473 discloses a process for the preparation of alkyl acrylates, such as methyl methacrylate, by the carboxylation of propadiene. Example 10 in the specification describes an experiment in which methyl methacrylate is prepared by reacting a mixture of propadiene and propyne with carbon monoxide and methanol in the presence of a relatively inactive carboxylation catalyst. Both the propadiene and the propyne are converted into methyl methacrylate. Surprisingly, it has now been found that propadiene poisons carboxylation catalysts in the carboxylation of propyne and methanol to give methyl methacrylate. Moreover, the poisoning effect of propadiene appears to increase as the intrinsic activity of the carboxylation catalyst for propyne carboxylation increases.

It is thus an object of the invention to provide a process for the preparation of an alkyl methacrylate which can be carried out at industrial scale and at low cost. It is a further object of the invention to provide a process which uses large quantities of propyne in a quality in which it may be easily supplied. Finally, it is an object of the invention to provide an industrial scale process which can make use of high activity carboxylation catalysts.

SUMMARY OF THE INVENTION

Accordingly, the invention provides a process for the preparation of an alkyl methacrylate, which comprises: a) selectively removing propadiene from a $C_3$ mixture comprising a mixture of propyne and propadiene that has been obtained from an ethene cracker, a catalytic cracker or an LPG-dehydrogenation process, to afford a propyne feed in which the ratio of propyne to propadiene is at least about 6:1, and b) contacting the thus-treated propyne feed with carbon monoxide and an alkanol in the presence of a carboxylation catalyst.

DETAILED DESCRIPTION OF THE INVENTION

Of the many potential sources of a propyne feed for the preparation of alkyl methacrylates, the cheapest appears to be the $C_3$-stream produced by an ethene cracker (also known as a naphtha cracker, a gas oil cracker and/or an LPG cracker), a catalytic cracker or an LPG (liquefied petroleum gas)-dehydrogenation process. A characteristic of such a stream is that it comprises a mixture of propyne and propadiene in an approximate ratio of 1 to 1. At present, the mixture of propyne and propadiene is generally not separated, but is usually burned (either as a flare or as welding gas) or is hydrogenated to propene and propane.

The $C_3$-mixture used as the starting material in the process according to the invention is a by-product stream from an ethene cracker, a catalytic cracker or an LPG-dehydrogenation process which comprises a mixture of propyne and propadiene. Ethene crackers, catalytic crackers and LPG-dehydrogenation processes are well known.

An ethene cracker is a type of cracker in which ethene is prepared from hydrocarbon fractions such as naphtha, gas oil, LPG (preferably isobutane) or ethane by thermal cracking. A catalytic cracker is a cracker in which hydrocarbons are prepared by the catalytic cracking of hydrocarbon fractions such as heavy gas oil or vacuum distillates. An LPG-dehydrogenation process is a process in which propane is converted into propene, either thermally or catalytically. Each of these processes provides, among others, a $C_3$-stream consisting mainly of $C_3$-hydrocarbons, in particular propane, propene, propyne and propadiene. Preferably the $C_3$-mixture comprises a mixture of propyne and propadiene that has been obtained from an ethene cracker.

The $C_3$-mixture used in the process according to the invention may be a $C_3$-stream produced by an ethene cracker, a catalytic cracker or an LPG-dehydrogenation process. However, it is preferably a mixture derived from a $C_3$-stream by a process in which the concentration of the mixture of propyne and propadiene has been increased. For example, it may be a mixture derived from such a $C_3$-stream by distilling-off propane and/or propene, by selective scrubbing with a solvent and/or by adding more propyne and/or propadiene. More propyne and/or propadiene may be added, for example by way of a recycle to be described in greater detail hereinafter.

In some cases, it will be very convenient to combine mixtures of propyne and propadiene obtained from several different ethene crackers, catalytic crackers and/or LPG-dehydrogenation processes, which may be located at different refineries. Such mixtures will most conveniently be transported in concentrated form.

An attractive way of obtaining the $C_3$-mixture from an ethene cracker plant comprises taking at least part of the "crude" $C_3$-stream obtained from an already present depropaniser (a distillation column in which $C_3$-hydrocarbons are separated from higher hydrocarbons), bypassing the hydrogenator (where normally the propyne, propadiene and some propene are hydrogenated to a propane/propene mixture, whence the latter mixture is fed to a propane/propene splitter from which "polymer grade" propene is obtained as a top stream and essentially pure propane as a bottom stream) and introducing it directly into a propane/propene splitter. In this embodiment, it is advantageous to operate the splitter under slightly different conditions than when operating with hydrogenation as described above, to account for the fact that at least part of its feed still contains some propyne and/or propadiene, as it has not been subjected to a preliminary hydrogenation. It would then be operated such that the top stream of the splitter would still contain "polymer grade" propene, though in lesser yield, and some of the propene would leave the splitter at the bottom with a stream which consists mainly of propane and propene (about 70%) and further contains propadiene and propyne in roughly equimolar portions.

It is advantageous to minimize the amount of inert or quasi-inert materials in the propyne feed in order to maximize the throughput of a plant having a fixed capacity at a given catalyst activity. Thus, according to a preferred aspect of the invention, the mixture of propyne and propadiene in the $C_3$-mixture can be concentrated by selective scrubbing with a solvent, whereby a solvent stream containing the $C_3$-mixture is obtained. For example, the mixture of propyne and propadiene may have been obtained from the bottom effluenet of a propane/propene splitter which contains significant amounts of propane, propene, propyne and propadiene. The scrubbing is suitably carried out in a column under elevated pressure (2-20, preferably 6-12 bar) using countercurrent flows of an organic solvent and the bottom effluent of the propane/propene splitter, so that typically a stream consisting essentially of propane and propene (and <0.2% of propyne/propadiene) is removed as the overhead fraction.

The solvent which absorbs propyne and also propadiene at the elevated pressure employed, suitably comprises a polar organic solvent, such as an amide, e.g. dimethylformamide, dimethylacetamide or N-methylpyrrolidone; a nitrile such as acetonitrile; a sulfone such as sulfolane; or a mixture thereof. Dimethylformamide is particularly suitable. Another preferred extraction solvent is an alcohol such as methanol, which presents the advantage that it can be used as one of the reactants in the subsequent carboxylation reaction, and thus simplifies the management of the process.

The propadiene may be selectively removed by chemical means, such as by isomerization to propyne, and/or by physical means such as by distillation, preferably extractive distillation.

The isomerization of propadiene into propyne is a chemical equilibrium reaction and is well known in the art. The position of chemical equilibrium depends upon the temperature. Thus as the temperature is increased, the proportion of propadiene increases. At ambient temperature, the ratio of propyne to propadiene obtained by isomerization is approximately 9 to 1.

The isomerization is conveniently effected in the gas or liquid phase in the presence of an isomerization catalyst at a temperature in the range of from about −30° to about 100° C., preferably about 0° to about 40° C., more preferably about 10° to about 30° C., and at a pressure in the range from about 0.1 to about 100 bar, more preferably about 1 to about 20 bar.

Catalysts suitable for isomerizing propadiene into propyne are well known. For example, the isomerization catalyst may comprise an alkali metal or alkali metal oxide deposited on alumina, such as a composition obtainable by heating an alkali metal carbonate deposited on an alumina carrier, preferably $K_2CO_3$ on gamma alumina, in an inert atmosphere, or a composition obtainable by depositing at least one molten alkali metal on alumina, preferably the low melting eutectic mixture of potassium and sodium on alumina. Suitable isomerization catalyts are also described in Kirk-Othmer's Encyclopaedia of Chemical Technology, 2nd ed., Volume Supplement (1971), pages 547 to 556, and in U.S. Pat. No. 3,671,605.

In general, the activity of isomerization catalysts decreases with decreasing temperature. Accordingly, when it is desired to prepare a propyne feed in which the ratio of propyne to propadiene is $\geq 10$, especially $\geq 20$, it is preferable to remove propadiene from the $C_3$-mixture by physical separation means.

When propadiene has been removed by physical separation means it may then be reacted with carbon monoxide and an alkanol to afford alkyl methacrylate. However, it is preferably isomerized to a mixture of propyne and propadiene, and recycled to step a) or step b) of the process. Optionally, the product of the isomerization is subjected to a distillation to remove heavy ends prior to recycling to step a) or step b).

Extractive distillation is a method well known for removing one component from a mixture comprising two very similar components. Thus, for the removal of propadiene from a mixture of propyne and propadiene, the mixture of propyne and propadiene is dissolved in a polar organic solvent, and propadiene is removed as a gas (e.g. by stripping) leaving propyne dissolved in the solvent. Suitable solvents include amides, for example dimethyl formamide or N-methylpyrrolidone, nitriles such as acetonitrile, sulfones such as sulfolane and alcohols such as methanol. Dimethylformamide, N-methylpyrrolidone, methanol and mixtures thereof are preferred solvents.

It will be appreciated that by combining a physical separation step for the removal of propadiene with an isomerization step, all of the propyne and propadiene in the original $C_3$-mixture can in principle be converted into alkyl methacrylate. This combination of process steps therefore constitutes a particularly preferred aspect of the invention.

When the $C_3$-mixture has been obtained by scrubbing with a solvent, propadiene is advantageously removed by stripping from the propyne and propadiene containing solvent stream to afford the propyne feed. This stripping is possible because propadiene and propyne exhibit different volatilities and solubilities in solvents. The stripping may suitably take place in a column downstream of the main absorption column, employing indirect heat exchange in the bottom of the column. The propyne may then, if desired, be separated from the solvent in a further column. The stripping operation can be adjusted to a propadiene content in the propyne feed of almost zero.

In the process according to the invention, the molar concentration of propyne in the propyne feed preferably lies above about 35%, more preferably above about 50%, even more preferably above about 90%, most preferably at least about 99%. Thus the feed mixture preferably contains at most about 10% (molar) of propadiene and at least about 35% (molar) of propyne.

The propene feed preferably comprises at least about 50% (mass) of propyne and propadiene combined, more preferably at least about 60%, even more preferably at least about 80%. The propyne feed preferably comprises at least about 50%, especially at least about 90% (molar), of $C_3$-hydrocarbons.

In the process according to the invention, it is preferred to use a propyne feed in which the ratio of propyne to propadiene is at least about 8, particularly $\geq 20$, and especially $\geq 100$. With highly active carboxylation catalysts, it is preferable to use a propyne feed in which the ratio is $\geq 500$, more preferably $\geq 1000$, most preferably $\geq 10,000$.

The carboxylation catalyst used in the process according to the invention may be any catalyst having activity for the carboxylation of propyne. It is preferably a Group VIII metal catalyst, more preferably a palladium catalyst.

Preferably the carboxylation catalyst is based on a composition of a Group VIII (e.g. palladium) compound, a ligand (e.g. a monodentate or quasi-bidentate phosphine, arsine, stibine or a similar nitrogen compound) and an anion of a Broensted acid (from a salt, ester, anhydride or acid, and preferably not too strongly coordinating). A particularly preferred example of such a catalyst is based on a composition of a palladium (II) compound, an organic phosphine of formula $PR_3$ in which each R independently stands for an optionally substituted hydrocarbyl or heterocyclic group, and a non-hydrohalogenic Broensted acid having a $pK_A < 2$.

A hydrocarbyl group in an optionally substituted hydrocarbyl group is preferably an alkyl group, for example a $C_{1-6}$ alkyl group such as methyl, ethyl, propyl, isopropyl, butyl, isobutyl, or t-butyl, a cycloalkyl group, e.g. cyclopentyl or cyclohexyl, or an aryl group such as phenyl or naphthyl. Two R-groups may alternatively represent an optionally substituted alkylene chain.

A heterocyclic group in an optionally substituted heterocyclic group is preferably an aromatic group having an imino nitrogen, for example a pyridyl, pyrazinyl, quinolyl, isoquinolyl, pyrimidinyl, pyridazinyl, cinnolinyl, triazinyl, quinoxalinyl or quinazolinyl group. An imino nitrogen atom in an aromatic group having an imino nitrogen atom is preferably connected to phosphorus through a single bridging nitrogen atom, as for example in 2-pyridyl, 2-pyrazinyl, 2-quinolyl, 1-isoquinolyl, 3-isoquinolyl, 2-pyrimidinyl, 3-pyridazinyl, 3-cinnolinyl, 2-triazinly, 2-quinoxalinyl and 2-quinazolinyl.

Examples of optional substituents which may be present in an optionally substituted hydrocarbyl or heterocyclic group include halogen atoms, e.g. fluorine, chlorine or bromine; alkyl groups, i.e. methyl or ethyl; haloalkyl groups, e.g. trifluoromethyl; alkoxy groups, e.g. methoxy or ethoxy; haloalkoxy groups, e.g. trifluoromethoxy; acyl groups, e.g. acetyl; acyloxy groups, e.g. acetoxy; amino groups, e.g. dimethylamino; hydroxyl groups; nitrile groups; acylamino groups, e.g. acetamido; and aryl groups, e.g. phenyl.

A non-halogenic Broensted acid may be, for example, sulfuric acid, a sulfonic acid such as p-toluenesulfonic acid, naphthalenesulfonic acid, trifluoromethanesulfonic acid, chlorosulfonic acid, fluorosulfonic acid or a sulfonated ion exchange resin; a phosphoric acid such as orthophosphoric acid, pyrophosphoric acid or benzene phosphoric acid; a carboxylic acid such as trifluoroacetic acid; a perhalic acid such as perchloric acid; fluorosilicic acid; $HBF_4$; $HPF_6$ or $HSbF_6$.

Examples of such catalysts are mentioned in U.S. Pat. No. 4,739,109, the disclosure of which is incorporated herein by reference. Most preferable examples include combinations of (a) palladium acetate, (b) triphenylphosphine, tris(p-methoxyphenyl)phosphine, or diphenyl-2-pyridylphosphine, and (c) p-toluenesulfonic or trifluoroacetic acid.

The reaction between propyne, the alcohol and carbon monoxide is preferably effected at a temperature in the range of from about 20° to about 200° C., more preferably about 20° to about 80° C., and at a pressure in the range of from about 5 to about 70 bar. A separate solvent is not essential for the reaction. However, an ester of the alcohol may conveniently be used as solvent.

When the carboxylation catalyst is a Group VIII metal catalyst, it is preferred that the catalyst has a conversion activity in the absence of propadiene of at least about 100 g propyne/g of catalytic metal/hour, more preferably about 1,000 g propyne/g of catalytic metal/hour, preferably of at least about 5,000, more preferably of at least about 10,000 g propyne/g of catalytic metal/hour. This is equivalent roughly to a production of about 25 kg methacrylate/g catalytic metal/hour, where the catalytic metal is palladium and the methacrylate is methyl methacrylate.

The alkyl methacrylate which is the product of the present process is suitably an ester of an alcohol having up to 20, preferably 1 to 4 carbon atoms. Examples of alcohols are methanol, ethanol, propanol, iso-propanol, butanol, iso-butanol and tert-butanol. Most preferably the alkanol is methanol, thus giving methyl methacrylate as the product.

A suitable and attractive method for carrying out the carboxylation reaction involves combining the propyne feed with a mixture of fresh alkanol and a recycle stream of an methacrylate/alkanol azeotrope, and then feeding this combined feed stream into the reactor simultaneously with (a solution of) the catalyst and carbon monoxide.

This process is further described using methanol as the preferred alkanol feed. Very suitably the propyne feed is brought into a mixing device, e.g. tank, to combine it with a mixture of fresh methanol and a recycle stream of a methyl methacrylate/methanol azeotrope, and is then fed into the reactor, and concomitant with that, the catalyst solution is also fed into the reactor. One could introduce the catalyst solution using the CO feed pipe or separately. The reactor effluent product stream is flashed isothermally and stripped of unreacted gases. This gas steam may be chilled (to about $-20°$ C.) to recondensed valuable low volatile components which are returned to the liquid feed. The uncondensed gas (mainly CO) is removed and used elsewhere, e.g. as a fuel. Any unreacted propyne present therein can be scrubbed out with methanol and recycled to the reactor. The liquid fraction, which contains product, catalyst residues and heavy ends, is fed into a distillation column.

The column top stream, which consists of an azeotrope of methyl methacrylate and methanol, is recycled to the feed mixing device and subsequently to the reactor. The bottom stream is suitably fed to a second distillation column. The top product from this column is pure methyl methacrylate, whereas the bottom product contains some methacrylate, catalyst residues and heavy ends. The latter methyl methacrylate may be recovered in a heavy ends stripper and returned to the second column. The concentrated residue may be worked up for reuse or for disposal in a responsible way.

The invention will now be illustrated in more detail by the following Examples. Example 1 illustrates a process in which a C₃-mixture typical of that of a C₃-steam from a cracker is converted into a propyne feed by scrubbing with a solvent followed by stripping off of propadiene. Example 2 illustrates a process in which propadiene is isomerized over an isomerization catalyst to afford propyne. Examples 3 and 4 illustrate the carboxylation of proyne to afford methyl methacrylate. The Comparative Examples demonstrate the poisoning effect of propadiene on the carboxylation of propyne.

EXAMPLE 1

In a calculated experiment, a fresh feed, consisting of 52.7 mole % propane, 1.6 mole % of propylene, 19.1 mole % of propadiene and 25.1 mole % of propyne and 1.5% of heavier hydrocarbons, is combined with a recycle stream from a propadiene isomerization reactor and fed to an absorption column. If necessary the feed is first sent to a distillation column to remove high boiling impurities. The combined mixture contains 45.4% propane, 10.5% propylene, 11.4% propadiene and 32.7% propyne.

In the absorber the combined mixture is contacted with DMF (dimethylformamide) (2.8 kg DMF/kg combined mixture). The absorber is operated at 8 bar and is provided with a reboiler and a condensor. The liquid top product consists of 96.8% of propane, 3.0% propylene, 0.2% of propadiene and propyne combined. The bottom product consists of 68.3% DMF, 4.8% propadiene and 14.2% propyne, 8.6% propane and 4.1% propylene.

This mixture is cooled to 35° C. and fed to a first reboiled stripper provided with a condensor, operating at 2.6 bar, where all the propane, propylene, propadiene and part of the propyne are stripped off, resulting in a bottom product consisting of 88.1% DMF and 11.9% methylacetylene with only 10 ppm propadiene. The top product, consisting of 38.2% propane, 18.3% propylene, 21.5% propadiene and 22% propyne is fed to the propadiene isomerization reactor containing an isomerization catalyst where part of the propadiene is converted to propyne, resulting in an effluent containing 4.4% propadiene and 39.1% propyne. This effluent is the recycle stream which is combined with the fresh feed.

The bottom product is fed to a second reboiled stripper equipped with a condensor operating at 1.6 propyne containing only 80 ppm propadiene. The bottom product consists of DMF containing 0.5% propyne, which, after being cooled, is used again in the first absorber. The purpose of the condensors in the strippers is not only to condense the hydrocarbon vapors, but also to remove DMF from the hydrocarbon product.

EXAMPLE 2

Preparation of Catalyst

A 20 % w potassium carbonate on alumina catalyst was prepared as follows: 250 g of 1/16" cylindrical gamma-Al₂O₃ (gamma-alumina) extrudates (pore volume=0.7 ml/g) were activated during 16 hours at 500° C. 50 g of K₂CO₃ (potassium carbonate, Baker analyzed) was dissolved in 150 ml of demineralized water at ambient temperature. 200 g of the activated gamma-Al₂O₃ was contacted with the K₂CO₃ solution and well mixed (incipient wetness method).

After impregnation the catalyst was dried at 125°–140° C. for 16 h. Prior to use the thus obtained 20% w K₂CO₃ on gamma-Al₂O₃ was activated under nitrogen at 575° C. during 24 hours.

Isomerization of Propadiene

Propadiene was isomerized to propyne in a packed bed reactor containing activated K₂CO₃ on gamma-Al₂O₃ catalyst according to the following procedure: A 0.9 cm i.d. stainless steel tube reactor was filled with 2.0 g of K₂CO₃ on gamma-Al₂O₃ catalyst particles. The catalyst was activated according to the temperature treatment described above.

The reactor was fitted in an experimental set-up and a feed mixture of liquefied C₃- and C₄-hydrocarbons was pumped over the catalyst. The feed contained 15% v propadiene, 22% v propyne, 49% v propene, 5% v propane, 3% v 1,3-butadiene and some minor amounts of other C₃- and C₄-hydrocarbons.

At liquid hourly space velocities up to 10 l (feed)/l (reactor).hr propyne/propadiene isomerization equilibrium was established. The propyne and propadiene concentrations in the reaction product from the above described feed amounted 33.7% v and 3.3% v, when the reaction was carried out at 25° C.

EXAMPLE 3

A 250 ml magnetically stirred autoclave was filled with 0.1 mmol palladium acetate, 1 mmol tri(p-trifluoromethylphenyl)phosphine, 1 mmol methanesulfonic acid, 10 ml methanol and 40 ml anisole.

Air was then evacuated from the autoclave, and then 30 ml propyne was added. Then carbon monoxide was added to a pressure of 20 bar. The autoclave was then sealed and heated to 90° C. Upon completion of the reaction, the contents of the autoclave were analyzed by gas liquid chromatography. The reaction rate was calculated to be 40 g propyne/g Pd/hour.

COMPARATIVE EXAMPLE A

The method of Example 3 was repeated, but using 15 ml propyne and 15 ml allene. The reaction rate was calculated to be 4 g propyne and allene/g Pd/hour.

EXAMPLE 4

A 300 ml magnetically stirred stainless steel autoclave was successively filled with 0.025 mmol palladium(II) acetate, 1 mmol bis(6-methyl-2-pyridyl)-phenylphosphine, 2 mmol paratoluenesulfonic acid, 30 ml N-methylpyrrolidone and 30 ml methanol. Air was evacuated from the autoclave, whereupon 25 ml propyne was added. Subsequently, carbon monoxide was added to a pressure of 60 bar. The autoclave was sealed and heated to a temperature of 80° C. After a reaction time of 1.5 hours at 80° C. a specimen of the contents was analyzed by means of gas liquid chromatography. The mean conversion rate was calculated to be 7500 g propyne/g Pd/hour.

COMPARATIVE EXAMPLE B

The method of Example 4 was repeated, but using 20 ml propyne and 10 ml propadiene instead of 25 ml propyne, and heating to 60° C. No reaction was observed. The autoclave was then heated to 80° C. Again, no reaction was observed. The autoclave was finally heated to 100° C. Reaction was then observed. The reaction time was 5 hours. The mean conversion rate was calculated to be only 200 g propyne and propadiene/g Pd/hour.

We claim:

1. In a process for the preparation of an alkyl methacrylate by reacting propyne, carbon monoxide and an alkanol in the presence of a palladium carboxylation catalyst, the improvement which comprises:
   (a) providing a by-product stream from an ethene cracker, a catalytic cracker or an LPG-dehydrogenation process comprising a $C_3$ mixture comprising propyne and propadiene;
   (b) subjecting said $C_3$ mixture to extractive distillation or stripping to remove a sufficient amount of the propadiene to form a propyne feed having a molar ratio of propyne to propadiene of at least about 100:1; and
   (c) reacting the propyne in said propyne feed with carbon monoxide and an alkanol in the presence of a palladium carboxylation catalyst under conditions effective to produce the alkyl methacrylate.

2. In a process for the preparation of an alkyl methacrylate by reacting propyne, carbon monoxide and an alkanol in the presence of a carboxylation catalyst comprising a Group VIII metal compound, a ligand and an anion of a Bronsted acid, the improvement which comprises:
   (a) providing a by-product stream from an ethene cracker, a catalytic cracker or an LPG-dehydrogenation process comprising a $C_3$ mixture comprising propyne and propadiene;
   (b) concentrating said $C_3$ mixture to provide a concentrated stream having an increased concentration of propyne and propadiene in the $C_3$ mixture;
   (c) subjecting said concentrated stream to extractive distillation or stripping to remove a portion of the propadiene and to produce a propyne feed having a molar ratio of propyne to propadiene of at least 100:1;
   (d) contacting any removed propadiene with an isomerization catalyst to provide a recycle stream;
   (e) passing said recycle stream to at least one of steps (b), (c), (d) and (f); and
   (f) passing said propyne feed to a reaction zone and contacting the propyne therein with carbon monoxide and an alkanol in the presence of a palladium carboxylation catalyst under conditions effective to produce the alkyl methacrylate.

3. The process of claim 1 in which $C_3$-mixture comprises a by-product stream from an ethene cracker.

4. The process of claim 2 in which said by-product stream is the product of passing at least part of a $C_3$-stream from a depropanizer to a propane/propene splitter and recovering a bottom effluent.

5. The process of claim 1 in which the mixture of propyne and propadiene in the $C_3$-mixture has been concentrated by selective scrubbing of the $C_3$-mixture with a solvent, whereby a solvent stream comprising propyne and propadiene is obtained.

6. The process of claim 5 in which the solvent is selected from the group consisting of dimethylformamide, N-methyl-pyrrolidone, methanol and mixtures thereof.

7. The process of claim 6 in which propadiene is selectively removed by stripping from the solvent stream.

8. The process of claim 7 comprising contacting said removed propadiene with an isomerization catalyst under conditions effective for conversion of propadiene to propyne, and recycling the isomerization product to at least one of step a) and step b).

9. The process of claim 8 in which the isomerization catalyst comprises at least one of an alkali metal on alumina and an alkali metal oxide on alumina.

10. The process of claim 1 in which propadiene is selectively removed by extractive distillation.

11. The process of claim 9 comprising contacting said removed propadiene with an isomerization catalyst under conditions effective for conversation of propadiene to propyne, and recycling the isomerization product to at least one of step a) and step b).

12. The process of claim 1 in which the propyne feed comprises at least 99% (mass) of propyne.

13. The process of claim 1 in which the alkanol is methanol.

14. The process of claim 2 in which the by-product stream comprises the product of introducing at least part of a $C_3$-hydrocarbon stream from a depropanizer directly into a propane/propene splitter and recovering the bottom effluent.

15. The process of claim 2 wherein the $C_3$-mixture is concentrated by selective scrubbing with a solvent.

16. The process of claim 2 wherein the $C_3$-mixture is concentrated by adding the recycled isomerized product thereto.

17. The process of claim 2 wherein the propadiene is removed by contacting the $C_3$-mixture with an isomerization catalyst at a temperature within the range of from about $-30°$ to about 100° C. and a pressure within the range of about 0.1 to about 100 bar.

18. The process of claim 20 in which the isomerization catalyst comprises at least member selected from the group consisting of an alkali metal on alumina and an alkali metal oxide on alumina.

19. The process of claim 2 wherein the propadiene is selectively removed by extractive distillation.

20. The process of claim 2 wherein the ratio of propyne to propadiene in the propyne feed is at least about 500:1.

21. The process of claim 2 in which the carboxylation catalyst comprises a Group VIII metal compound, a ligand, and an anion of a Broensted acid.

22. The process of claim 21 in which the Group VIII metal compound is palladium.

23. The process of claim 22 in which the ligand is an organic phosphine.

24. The process of claim 23 in which the Broensted acid is an non-halogenic Broensted acid having a $pK_A < 2$.

25. The process of claim 24 in which the propyne feed is contacted at a temperature within the range of about 20° to about 200° C. and a pressure within the range of from about 5 to about 70 bar.

* * * * *